(12) United States Patent
Selent et al.

(10) Patent No.: US 7,161,020 B2
(45) Date of Patent: Jan. 9, 2007

(54) PHOSPHITE COMPOUNDS AND NOVEL PHOSPHITE METAL COMPLEXES

(75) Inventors: Detlef Selent, Berlin (DE); Armin Boerner, Rostock (DE); Cornelia Borgmann, Recklinghausen (DE); Dieter Hess, Marl (DE); Klaus-Diether Wiese, Haltern am See (DE)

(73) Assignee: Oxeno Olefinchemie GmbH, Marl (DE)

( * ) Notice: Subject to any disclaimer, the term of this patent is extended or adjusted under 35 U.S.C. 154(b) by 158 days.

(21) Appl. No.: 10/485,811

(22) PCT Filed: Aug. 13, 2002

(86) PCT No.: PCT/EP02/09050

§ 371 (c)(1),
(2), (4) Date: Feb. 10, 2004

(87) PCT Pub. No.: WO03/016321

PCT Pub. Date: Feb. 27, 2003

(65) Prior Publication Data

US 2004/0236133 A1    Nov. 25, 2004

(30) Foreign Application Priority Data

Aug. 16, 2001  (DE) ............................... 101 40 086

(51) Int. Cl.
*C07F 9/02* (2006.01)
(52) U.S. Cl. .................... 558/153; 558/77; 558/78; 502/104
(58) Field of Classification Search ............... 558/153, 558/77, 78; 502/104
See application file for complete search history.

(56) References Cited

U.S. PATENT DOCUMENTS

| | | | |
|---|---|---|---|
| 4,668,651 A | 5/1987 | Billig et al. | |
| 4,748,261 A | 5/1988 | Billig et al. | |
| 4,885,401 A | 12/1989 | Billig et al. | |
| 5,312,996 A | 5/1994 | Packett | |

FOREIGN PATENT DOCUMENTS

| | | |
|---|---|---|
| EP | 155 508 | 9/1985 |
| EP | 214 622 | 3/1987 |
| EP | 472 071 | 2/1992 |
| EP | 1 201 675 | 5/2002 |
| EP | 1201675 | 5/2002 |
| NL | 6514392 | 5/1966 |

OTHER PUBLICATIONS

Siedentop e t al., The Synthesis and Complexation of Spacer Modified Phosphorylated Glucose Derivatives, Z. Naturforsch, 55 b, 956-960, (Jul. 20, 2000).*

Shadid et al., The Synthesis of Cytokinin Phosphates, Tetrahedron (1990), 46 (3), 901-912.*

Selent D et al: "New Phosphorus Ligands for the Rhodium-Catalyzed Isomerization/Hydroformylation of Internal Octenes" Angewandte Chemie, International Edition, Verlag Chemie. Weinheim, DE, vol. 40, No. 9 May 4, 2001, pp. 1696-1698 XP001009251 ISSN: 0570-0833 Liganden 2-7 p. 1696, col. 2 -p. 1698, col. 1; table 1.

Siedentop T et al: "Synthese Und Komplexierung Phosphorylierter Spacer-Modifizierter Glucosederivate Synthesis and Complexation of Spacer Modified Phosphorylated Glucose Derivatives" Zeitschrift Fur Naturforschung, Teil B: Anorganische Chemie, Organische Chemie, Verlag Der Zeitschrift Fur Naturforschung. Tubingen, DE, vol. 55, No. 10, 2000, pp. 956-960, XP001027205 ISSN: 0932-0776 Verbindurg 7 p. 957, col. 1-p. 959, col. 2 Verbindung 9 p. 958, col. 1-p. 960, col. 1 Einleitung p. 956, col. 1-col. 2.

Shadid B et al: "The Synthesis of Cytokinin Phosphatases" Tetrahedron, Elsevier Science Publishers, Amsterdam, NL, vol. 46, No. 3, 1990, pp. 901-912, XP002186808 ISSN: 0040-4020 Verbindung 14.

Database CA [Online] Chemical Abstracts Service, Columbus, Ohio, US; Mironov, V. F. et al: "Behavior of fluoroalkyl phosphites in reactions with sulfur chlorides" retrieved from STN Database accession No. 122:187680 XP002216984 figure 31 figure 30 & Zhurnal Obshchei Khimii (1994), 64 (8), 1358-61.

Selent D et al: "New Phosphorus Ligands for the Rhodium-Catalyzed Isomerization/Hydroformylation of Internal Octenes" Angewandte Chemie, International Edition, Verlag Chemie. Weinheim, DE, vol. 40, No. 9 May 4, 2001, pp. 1696-1698 XP001009251 ISSN: 0570-0833 Liganden 2-7 p. 1696, col. 2 -p. 1698, col. 1; table 1.

Siedentop T et al: "Synthese Und Komplexierung Phosphorylierter Spacer-Modifizierter Glucosederivate Synthesis and Complexation of Spacer Modified Phosphorylated Glucose Derivatives" Zeitschrift Fur Naturforschung, Teil B: Anorganische Chemie, Organische Chemie, Verlag Der Zeitschrift Fur Naturforschung. Tubingen, DE, vol. 55, No. 10, 2000, pp. 956-960 XP001027205 ISSN: 0932-0776 Verbindung 7 p. 957, col. 1-p. 959, col. 2 Verbindung p p. 958, col. 1-p. 960, col. 1 Einleitung p. 956, col. 1-col. 2.

(Continued)

*Primary Examiner*—Johann Richter
*Assistant Examiner*—Chukwuma Nwaonicha
(74) *Attorney, Agent, or Firm*—Oblon, Spivak, McClelland, Maier & Neustadt, P.C.

(57) ABSTRACT

Phosphites of the formula I

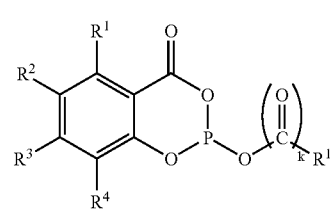

and phosphite-metal complexes, their preparation and their use in catalytic reactions, in particular in processes for the hydroformylation of olefins, are described.

14 Claims, No Drawings

OTHER PUBLICATIONS

Shadid B et al: "The Synthesis of Cytokinin Phosphatases" Tetrahedron, Elsevier Science Publishers, Amsterdam, NL, vol. 46, No. 3, 1990, pp. 901-912, XP002186808 ISSN: 0040-4020 Verbindung 14.

Database CA [Online] Chemical Abstracts Service, Columbus, Ohio, US; Mironov, V. F. et al: "Behavior of fluoroalkyl phosphites in reactions with sulfur chlorides" retrieved from STN Database accession No. 122:187680 XP002216984 figure 31 figure 30 & Zhurnal Obshchei Khimii (1994), 64 (8), 1358-61.

Database Crossfire Beilstein [Online] Beilstein Institut zur Foerderung der Chemischen Wissenschaften, Frankfurt am Main, DE; Database accession No. BRN 4874849; BRN 4886067 XP002216985 abstract & Mironov, V.F.: Izv. Aksd. Nauk. SSR SER KHIM.; RU, No. 3, 1993, pp. 565-567.

Database CA [Online] Chemical Abstracts Service, Columbus, Ohio, US; Ludwig, Janos et al: "Stereospecific synthesis of guanosine 5'-0-(1,2-dithiotriphosphates)" retrieved from STN Database accession No. 115:183763 XP002216986 Verbindung 32 abstract & Journal of Organic Chemistry (1991), 56(20), 5860-5.

Database Crossfire Beilstein [Online] Beilstein Institut zur Foerderung der Chemischen Wissenschaften, Frankfurt am Main, DE; Database accession No. BRN 8602957 XP002216987 abstract & Schoetzau, Th. et al.: J. Chem. Soc. Perkin Trans. 1, No. 9, 2000, pp. 1411-1416.

Database Crossfire Beilstein [Online] Beilstein Institut zur Foerderung der Chemischen Wissenschaften, Frankfurt am Main, DE; Database accession No. BRN 8519330 BRN 8532363 BRN 8530950 XP002216988 abstract & Schoetzau, Th. et al.: Synthesis, vol. 5, 2000, pp. 707-713.

Database Crossfire Beilstein [Online] Beilstein Institut zur Foerderung der Chemischen Wissenschaften, Frankfurt am Main, DE; Database accession No. BRn8530185 BRN 8524530 Xp002216989 abstract & Wojczewski, Ch. et al.: Synthesis. No. 1, 2000, pp. 149-153.

Database Crossfire Beilstein [Online] Beilstein Institut zur Foerderung der Chemischen Wissenschaften, Frankfurt am Main, DE; Database accession No. BRN 8592202 BRN 8605310 XP002216990 abstract & Wojczewski, Ch. et al.: Helv. Chim. Acta, vol. 83, No. 6, 2000, pp. 1268-1277.

Database Crossfire Beilstein [Online] Beilstein Institut zur Foerderung der Chemischen Wissenschaften, Frankfurt am Main, DE; Database accession No. BRN 5446652 XP002216991 abstract & Mironov, V.F. et al.: Zh. Obshch. Kim. RU, vol. 61, No. 10, 1991, pp. 2150-2154.

Database CA [Online] Chemical Abstracts Service, Columbus, Ohio, US; Kirpichnikov, P.A. et al: "Phosphorous acid esters as colorless stabilizers of low-pressure polyethylene" retrieved from STN Database accesssion No. 73:15657 XP002216992 cited in the application Verbindung 37 abstract & Vysokomol. Soedin., Ser. B (1970), 12(3), 189-92.

Database Crossfire Beilstein [Online] Beilstein Institut zur Foerderung der Chemischen Wissenschaften, Frankfurt am Main, DE; Database accession No. BRN 2660456; BRN 2662683; BRN 2662684; BRN 2664377 XP002226542 abstract & Nesterow, Sabirowa: J. Gen. Chem. USSR (Engl. Transl.), vol. 35, 1965, p. 1967.

Database Crossfire Beilstein [Online] Beilstein Institut zur Foerderung der Chemischen Wissenschaften, Frankfurt am Main, DE; Database accession No. BRN 2657140; Reaction ID 5068507 XP002226543 abstract & Munoz, A. et al. : J. Org. Chem., vol. 61, No. 17, 1996, pp. 6015-6017.

Database Crossfire Beilstein [Online] Beilstein Institut zur Foerderung der Chemischen Wissenschaften, Frankfurt am Main, DE; Database accession No. BRN 2665957 XP002226544 abstract & Cade, J.A. et al.: J. Chem. Soc., 1960, pp. 1249-1253.

* cited by examiner

PHOSPHITE COMPOUNDS AND NOVEL PHOSPHITE METAL COMPLEXES

The present invention relates to new phosphite compounds and new phosphite-metal complexes, and to their use in catalytic reactions.

The reaction of olefin compounds, carbon monoxide and hydrogen in the presence of a catalyst to form the aldehydes having one more carbon atom is known as hydroformylation (oxo process). Catalysts used in these reactions are frequently compounds of transition metals of groups 8 to 10 of the Periodic Table of the Elements, in particular compounds of rhodium and of cobalt. Compared to catalysis using cobalt compounds, hydroformylation using rhodium compounds generally offers the advantage of higher selectivity and is thus usually more economical. In the case of rhodium-catalyzed hydroformylation, use is usually made of complexes which comprise rhodium and preferably trivalent phosphorus compounds as ligands. Known ligands are, for example, compounds from the classes of phosphines, phosphites and phosphonites. An overview of the hydroformylation of olefins may be found in B. CORNILS, W. A. HERRMANN, "Applied Homogeneous Catalysis with Organometallic Compounds", Vol. 1&2, VCH, Weinheim, N.Y., 1996.

Each catalyst system (cobalt or rhodium) has its specific advantages. Depending on the starting material and target product, different catalyst systems are used. If rhodium and triphenylphosphine are employed, α-olefins can be hydroformylated at low pressures. As phosphorus-containing ligand, it is usual to employ triphenylphosphine in excess. A high ligand/rhodium ratio is necessary to increase the selectivity of the reaction to the commercially desirable n-aldehyde product. U.S. Pat. No. 4,694,109 and U.S. Pat. No. 4,879,416 relate to bisphosphine ligands and their use in the hydroformylation of olefins at low synthesis gas pressures. High activities and high n/i selectivities are achieved using ligands of this type, particularly in the hydroformylation of propene.

WO-A-95/30680 describes bidentate phosphine ligands and their use in catalysis, including hydroformylation reactions.

Ferrocene-bridged bisphosphines are disclosed, for example, in U.S. Pat. No. 4,169,861, U.S. Pat. No. 4,201,714 and U.S. Pat. No. 4,193,943 as ligands for hydroformylations.

The disadvantage of bidentate phosphine ligands is their relatively complicated preparation. For this reason, it is often not economically viable to use such systems in industrial processes.

Rhodium-monophosphite complexes are suitable catalysts for the hydroformylation of branched olefins having internal double bonds, but the selectivity to terminally hydroformylated compounds is low. EP-A-0 155 508 discloses the use of bisarylene-substituted monophosphites in the rhodium-catalyzed hydroformylation of sterically hindered olefins, e.g. isobutene.

Rhodium-phosphite complexes catalyze the hydroformylation of linear olefins having terminal and internal double bonds to form predominantly terminally hydroformylated products, but branched olefins having internal double bonds are reacted to only a small extent. When coordinated to a transition metal center, these phosphites give catalysts of increased activity, although the operating life behavior of these catalyst systems is unsatisfactory, partly because of the hydrolysis sensitivity of the phosphite ligands. Considerable improvements were able to be achieved by use of substituted bisaryldiols as starting materials for the phosphite ligands, as described in EP-A-0 214 622 or EP-A-0 472 071.

According to the literature, the rhodium complexes of these ligands are extremely active hydroformylation catalysts for α-olefins. U.S. Pat. No. 4,668,651, U.S. Pat. No. 4,748,261 and U.S. Pat. No. 4,885,401 describe polyphosphite ligands by means of which α-olefins and also 2-butene can be converted with high selectivity into the terminally hydroformylated products. In U.S. Pat. No. 5,312,996, bidentate ligands of this type are also used for the hydroformylation of butadiene.

Although the phosphites mentioned are good complexing ligands for rhodium-containing hydroformylation catalysts, it is desirable to discover further readily preparable phosphites to achieve further improvements in their effectiveness, for example in hydroformylation.

Phosphites having salicylic acid building blocks of the formula A

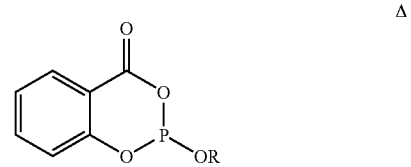

where R=alkyl, aryl, aralkyl, alkenyl, cycloalkyl, acyl, COPh, have been described as stabilizers for plastics in the patents JP 06025493, JP 2000038487 and JP 10081801.

P. A. Kirpichnikov et al. demonstrate the stabilizing properties of phosphites having salicylic acid building blocks in the Russian Journal Vysokomol. Soedin., Ser. B (1970), 12 (3), 189–192.

It has surprisingly been found that phosphites of the formula I

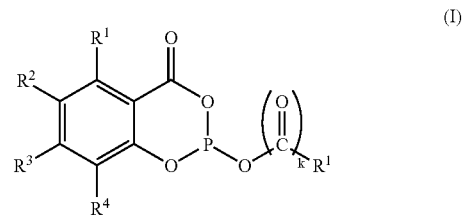

where $R^I$ is selected from among monovalent substituted or unsubstituted aliphatic, alicyclic, aromatic, heteroaromatic, mixed aliphatic-alicyclic, mixed aliphatic-aromatic, heterocyclic and mixed aliphatic-heterocyclic hydrocarbon radicals having from 1 to 50 carbon atoms, $R^1$, $R^2$, $R^3$ and $R^4$ are each selected independently from among monovalent substituted or unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radicals having from 1 to 50 carbon atoms, H, F, Cl, Br, I, —$CF_3$, —$CH_2(CF_2)_jCF_3$ where j=0–9, —$OR^9$, —$COR^9$, —$CO_2R^9$, —$CO_2M$, —$SR^9$, —$SO_2R^9$, —$SOR^9$, —$SO_3R^9$, —$SO_3M$, —$SO_2NR^9R^{10}$, —$NR^9R^{10}$, —$N=CR^9R^{10}$, where $R^9$ and $R^{10}$ are selected independently from among H, monovalent substituted or unsubstituted aliphatic and aromatic hydrocarbon radicals having from 1 to 25 carbon atoms and M is an alkali metal ion, formally half an alkaline earth metal ion, an ammonium ion or phosphonium ion, or adjacent radicals $R^1$ to $R^4$ together form a fused substituted or unsubstituted aromatic, heteroaromatic, aliphatic, mixed aromatic-aliphatic or mixed heteroaromatic-aliphatic ring system;

and k=0 or 1, or a phosphite-metal complex comprising a metal of group 4, 5, 6, 7, 8, 9 or 10 of the Periodic Table of the Elements and one or more of the phosphites of the formula I can be used in catalysis.

The present invention is preferably directed at the use of the phosphites or the phosphite-metal complexes in homogeneous catalysis, in particular in the hydroformylation of olefins. The invention also provides a process for the hydroformylation of olefins.

A further aspect of the present invention is the abovementioned phosphite-metal complexes. The invention further provides phosphites of the formula 1, with the proviso that when $R^1$, $R^2$, $R^3$ and $R^4$ are each an H atom and k=0, $R^I$ is not an alkyl, aryl, aralkyl, alkenyl or cycloalkyl group, and when $R^1$, $R^2$, $R^3$ and $R^4$ are each an H atom and k=1, $R^I$ is not an alkyl or aryl group.

In a preferred phosphite, the radical $R^I$ of the phosphite is selected from among aromatics and heteroaromatics which are unsubstituted or substituted by at least one radical selected from among aliphatic, alicyclic, aromatic, heteroaromatic, mixed aliphatic-alicyclic, mixed aliphatic-aromatic, heterocyclic, mixed aliphatic-heterocyclic hydrocarbon radicals having from 1 to 25 carbon atoms, F, Cl, Br, I, —$CF_3$, —$CH_2(CF_2)_jCF_3$ where j=0–9, —$OR^9$, —$COR^9$, —$CO_2R^9$, —$CO_2M$, —$SR^9$, —$SO_2R^9$, —$SOR^9$, —$SO_3R^9$, —$SO_3M$, —$SO_2NR^9R^{10}$, —$NR^9R^{10}$ or —$N=CR^9R^{10}$, where $R^9$, $R^{10}$ and M are as defined above.

In a likewise preferred phosphite, the radical $R^I$ is selected from among aromatics and heteroaromatics which have fused-on aromatic, heteroaromatic and/or aliphatic rings which are unsubstituted or substituted by at least one radical selected from among aliphatic, alicyclic, aromatic, heteroaromatic, mixed aliphatic-alicyclic, mixed aliphatic-aromatic, heterocyclic, mixed aliphatic-heterocyclic hydrocarbon radicals having from 1 to 25 carbon atoms, F, Cl, Br, I, —$CF_3$, —$CH_2(CF_2)_jCF_3$ where j=0–9, —$OR^9$, —$COR^9$, —$CO_2R^9$, —$CO_2M$, —$SR^9$, —$SO_2R^9$, —$SOR^9$, —$SO_3R^9$, —$SO_3M$, —$SO_2NR^9R^{10}$, —$NR^9R^{10}$ or —$N=CR^9R^{10}$, where $R^9$, $R^{10}$ and M are as defined above.

Preference is also given to using a phosphite whose radicals $R^1$ to $R^4$ together form a fused aromatic, heteroaromatic, aliphatic, mixed aromatic-aliphatic or mixed heteroaromatic-aliphatic ring system which is unsubstituted or is substituted by at least one radical selected from among aliphatic, alicyclic, aromatic, heteroaromatic, mixed aliphatic-alicyclic, mixed aliphatic-aromatic, heterocyclic, mixed aliphatic-heterocyclic hydrocarbon radicals having from 1 to 50 carbon atoms, F, Cl, Br, I, —$CF_3$, —$CH_2(CF_2)_j$ $CF_3$ where j=0–9, —$OR^9$, —$COR^9$, —$CO_2R^9$, —$CO_2M$, —$SR^9$, —$SO_2R^9$, —$SOR^9$, —$SO_3R^9$, —$SO_3M$, —$SO_2NR^9R^{10}$, —$NR^9R^{10}$ or —$N=CR^9R^{10}$, where $R^9$, $R^{10}$ and M are as defined above.

Representative phosphite ligands of the formula I for use according to the invention are:

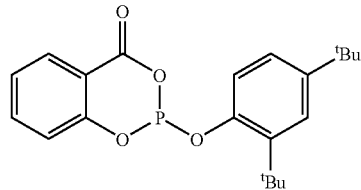

(A)

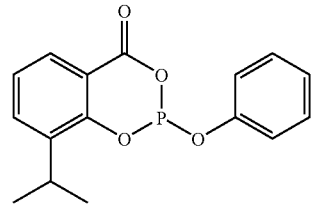

(B)

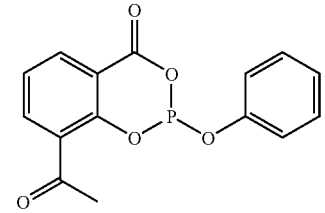

(C)

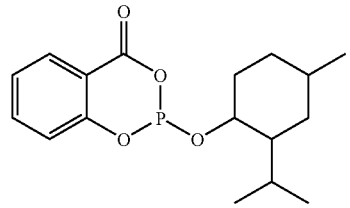

(D)

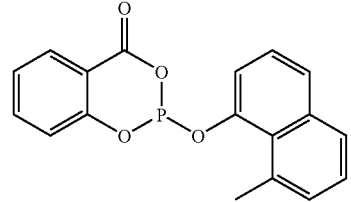

(E)

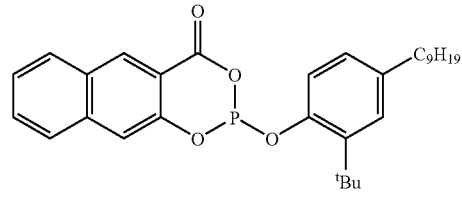

(F)

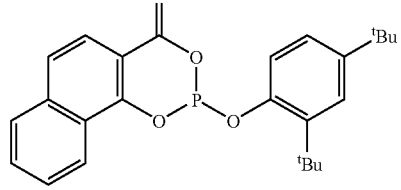

(G)

(H) 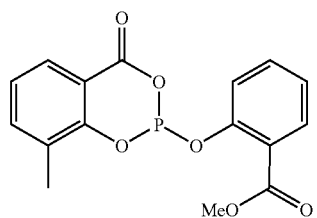

(J) 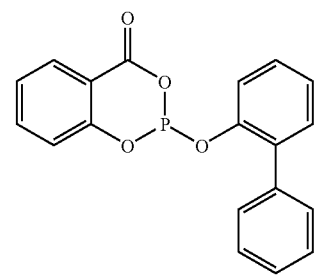

(K) 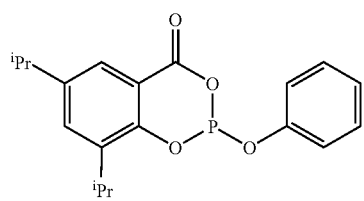

(L) 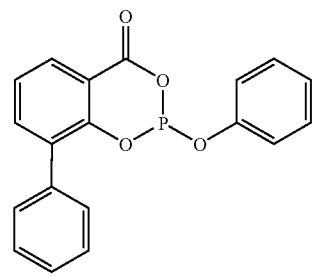

(M) 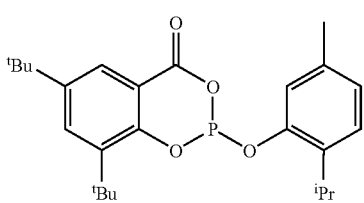

(N) 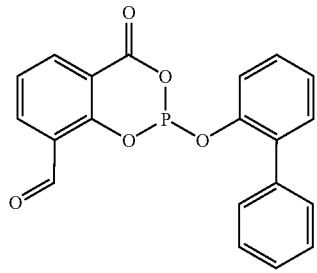

(O) 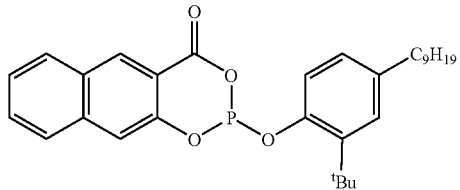

(P) 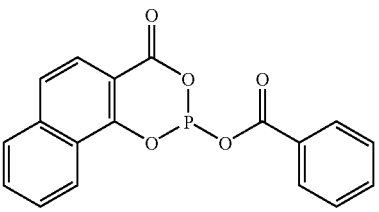

(Q) 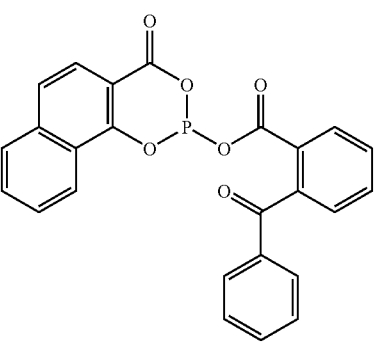

(S) 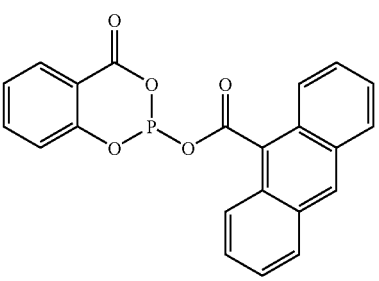

(T) 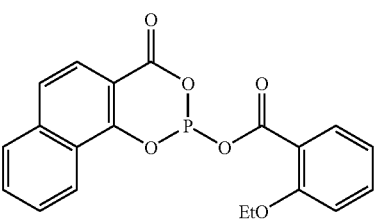

The phosphites for use according to the invention can be prepared by a sequence of reactions of phosphorus halides with alcohols, carboxylic acids and/or α-hydroxyarylcarboxylic acids in which halogen atoms on the phosphorus are replaced by oxygen groups. The basic procedure will be illustrated by way of example for a route to compounds of the formula I:

In a first step, an α-hydroxyarylcarboxylic acid is reacted with a phosphorus trihalide $PX_3$, e.g. $PCl_3$, $PBr_3$ or $PJ_3$, preferably phosphorus trichloride $PCl_3$, in the presence of a base which is preferably used in an equivalent or catalytic amount to form a halodioxaphosphorinone (1).

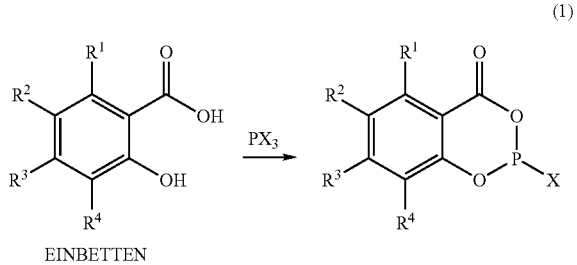

(1)

EINBETTEN

In a second reaction step, the halodioxaphosphorinone (1) is reacted with an alcohol HO—$R^I$ or a carboxylic acid HOOC—$R^I$ in the presence of a base which is preferably used in an equivalent or catalytic amount to give the desired phosphite of the formula (I) in which $R^I = R^{II}$. In the case of the reaction with an alcohol, k in the phosphite of the formula (I) is 0, while in the case of the reaction with a carboxylic acid, k is 1.

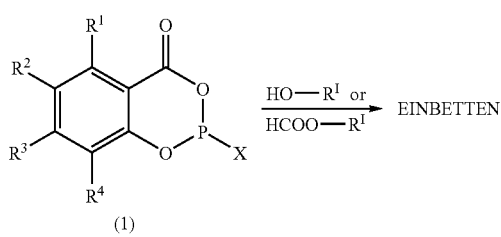

(1)

EINBETTEN

The radicals $R^1$ to $R^4$ and $R^I$ are as defined above.

Since the alcohols or carboxylic acids used and their downstream products are frequently solid, the reactions are generally carried out in solvents. Solvents used are aprotic solvents which react neither with the alcohols or carboxylic acids nor with the phosphorus compounds. Examples of suitable solvents are tetrahydrofuran, ethers such as diethyl ether or MTBE (methyl tert-butyl ether) and aromatic hydrocarbons such as toluene.

The reaction of phosphorus halides with alcohols forms a hydrogen halide which is bound by added bases in equivalent or catalytic amounts. Examples of such bases are tertiary amines such as triethylamine, pyridine or N-methylpyrrolidinone. It is sometimes also useful to convert the alcohols into metal alkoxides prior to the reaction, for example by reaction with sodium hydride or butyllithium.

The phosphites are suitable ligands for complexing metals of groups 4, 5, 6, 7, 8, 9 and 10 of the Periodic Table of the Elements. The complexes may contain one or more phosphite ligands and possibly further ligands and are suitable as catalysts, preferably in homogeneous catalysis. Examples of suitable metals are rhodium, cobalt, iridium, nickel, palladium, platinum, iron, ruthenium, osmium, chromium, molybdenum and tungsten. The complexes with metals of groups 8, 9 and 10 are especially useful as catalysts for hydroformylation, carbonylation, hydrogenation and hydrocyanation reactions; particular preference is given to rhodium, cobalt, nickel, platinum and ruthenium. For example, the use of rhodium as catalyst metal gives particularly high catalytic activities in hydroformylation reactions. The catalyst metals are used in the form of salts or complexes, in the case of rhodium as, for example, rhodium carbonyls, rhodium nitrate, rhodium chloride, $Rh(CO)_2$ (acac) (acac=acetylacetonate), rhodium acetate, rhodium octanoate or rhodium nonanoate.

The active catalyst species for the homogeneous catalysis is formed from the phosphite ligands and the catalyst metal under reaction conditions, for instance in the case of hydroformylation, a carbonylhydridophosphite complex on contact with synthesis gas. The phosphites and, if desired, further ligands can be added to the reaction mixture in free form together with the catalyst metal (as salt or complex) to generate the active catalyst species in situ. It is also possible to use a phosphite-metal complex comprising the above-mentioned phosphite ligands and the catalyst metal as precursor for the actual catalytically active complex. These phosphite-metal complexes are prepared by reacting the appropriate catalyst metal of groups 4 to 10 in elemental form or in the form of a chemical compound with the phosphite ligand.

As additional ligands present in the reaction mixture, it is possible to use phosphorus-containing ligands, preferably phosphines, bisphosphites, phosphonites or phosphinites.

EXAMPLES OF SUCH LIGANDS ARE

Phosphines: triphenylphosphine, tris(p-tolyl)phosphine, tris(m-tolyl)phosphine, tris(o-tolyl)phosphine, tris(p-methoxyphenyl)phosphine, tris(p-dimethylaminophenyl)phosphine, tricyclohexylphosphine, tricyclopentylphosphine, triethylphosphine, tri-(1-naphthyl)phosphine, tribenzylphosphine, tri-n-butylphosphine, tri-t-butylphosphine.

Phosphites: trimethyl phosphite, triethyl phosphite, tri-n-propyl phosphite, tri-i-propyl phosphite, tri-n-butyl phosphite, tri-i-butyl phosphite, tri-t-butyl phosphite, tris(2-ethylhexyl) phosphite, triphenyl phosphite, tris(2,4-di-t-butylphenyl) phosphite, tris(2-t-butyl-4-methoxyphenyl) phosphite, tris(2-t-butyl-4-methylphenyl) phosphite, tris(p-cresyl) phosphite. In addition, sterically hindered phosphite ligands as described, inter alia, in EP-A-155 508, U.S. Pat. No. 4,668,651, U.S. Pat. No. 4,748,261, U.S. Pat. No. 4,769,498, U.S. Pat. No. 4,774,361, U.S. Pat. No. 4,835,299, U.S. Pat. No. 4,885,401, U.S. Pat. No. 5,059,710, U.S. Pat. No. 5,113,022, U.S. Pat. No. 5,179,055, U.S. Pat. No. 5,260,491, U.S. Pat. No. 5,264,616, U.S. Pat. No. 5,288,918, U.S. Pat. No. 5,360,938, EP-A-472 071, EP-A-518 241 and WO-A-97/20795 are also suitable ligands.

Phosphonites: methyldiethoxyphosphine, phenyldimethoxyphosphine, phenyldiphenoxyphosphine, 2-phenoxy-2H-dibenz[c,e][1,2]oxaphosphorine and its derivatives in which all or some of the hydrogen atoms are replaced by alkyl and/or aryl radicals or halogen atoms and ligands as are described in WO-A-98/43935, JP-A-09-268152 and DE-A-198 10 794 and in the German patent applications DE-A-199 54 721 and DE-A-199 54 510.

Useful phosphinite ligands are described, inter alia, in U.S. Pat. No. 5,710,344, WO-A-95/06627, U.S. Pat. No. 5,360,938 or JP-A-07-082281. Examples are diphenyl(phenoxy)phosphine and its derivatives in which all or some of the hydrogen atoms are replaced by alkyl and/or aryl radicals or halogen atoms, diphenyl(methoxy)phosphine and diphenyl(ethoxy)phosphine.

The phosphites or phosphite-metal complexes can be used in processes for the hydroformylation of olefins, preferably olefins having from 2 to 25 carbon atoms, to give the corresponding aldehydes. Preference is in this case given to using phosphite complexes with metals of transition group 8 as catalyst precursors.

In general, from 1 to 500 mol, preferably from 1 to 200 mol, more preferably from 2 to 50 mol, of the phosphite according to the invention are used per mole of metal of transition group 8.

Fresh phosphite ligand can be added to the reaction at any point in time in order to keep the concentration of free ligand constant.

The concentration of the metal in the reaction mixture is in the range from 1 ppm to 1000 ppm, preferably in the range from 5 ppm to 300 ppm, based on the total weight of the reaction mixture.

The hydroformylation reactions carried out using the phosphites of the invention or the corresponding metal complexes were carried out by known methods, as described, for example, in J. FALBE, "New Syntheses with Carbon Monoxide", Springer Verlag, Berlin, Heidelberg, N.Y., page 95 ff., (1980). The olefin compound(s) is(are) reacted in the presence of the catalyst with a mixture of CO and $H_2$ (synthesis gas) to form the aldehydes having one more carbon atom.

The reaction temperatures for a hydroformylation process using the phosphites or phosphite-metal complexes of the invention as catalyst are preferably in the range from 40° C. to 180° C., more preferably from 75° C. to 140° C. The pressures under which the hydroformylation proceeds are preferably 1–300 bar of synthesis gas, more preferably 10–64 bar. The molar ratio of hydrogen to carbon monoxide ($H_2$/CO) in the synthesis gas is preferably from 10/1 to 1/10 and more preferably from 1/1 to 2/1.

The catalyst or the ligand is homogeneously dissolved in the hydroformylation mixture comprising starting materials (olefins and synthesis gas) and products (aldehydes, alcohols, high boilers formed in the process). A solvent can be additionally used if desired.

Owing to their relatively high molecular weight, the phosphites of the invention have a low volatility. They can therefore be separated off easily from the more volatile reaction products. They have a sufficiently good solubility in customary organic solvents.

The starting materials for the hydroformylation are olefins or mixtures of olefins having from 2 to 25 carbon atoms and a terminal or internal C═C double bond. They can be linear, branched or cyclic and can also have a plurality of olefinically unsaturated groups. Examples are propene; 1-butene, cis-2-butene, trans-2-butene, isobutene, butadiene, mixtures of $C_4$-olefins; $C_5$-olefins such as 1-pentene, 2-pentene, 2-methyl-1-butene, 2-methyl-2-butene, 3-methyl-1-butene; $C_6$-olefins such as 1-hexene, 2-hexene, 3-hexene, the $C_6$-olefin mixture formed in the dimerization of propene (dipropene); $C_7$-olefins such as 1-heptene, further n-heptenes, 2-methyl-1-hexene, 3-methyl-1-hexene; $C_8$-olefins such as 1-octene, further n-octenes, 2-methylheptenes, 3-methylheptenes, 5-methyl-2-heptene, 6-methyl-2-heptene, 2-ethyl-1-hexene, the isomeric $C_8$-olefin mixture formed in the dimerization of butenes (dibutene); $C_9$-olefins such as 1-nonene, further n-nonenes, 2-methyloctenes, 3-methyloctenes, the $C_9$-olefin mixture formed in the trimerization of propene (tripropene); $C_{10}$-olefins such as n-decenes, 2-ethyl-1-octene; $C_{12}$-olefins such as n-dodecenes, the $C_{12}$-olefin mixture formed in the tetramerization of propene or the trimerization of butenes (tetrapropene or tributene), $C_{14}$-olefins such as n-tetradecenes, $C_{16}$-olefins such as n-hexadecenes, the $C_{16}$-olefin mixture formed in the tetramerization of butenes (tetrabutene) and also olefin mixtures prepared by cooligomerization of olefins having different numbers of carbon atoms (preferably from 2 to 4), if appropriate after separation into fractions having an identical or similar number of carbon atoms by distillation. It is likewise possible to use olefins or olefin mixtures which are produced by Fischer-Tropsch synthesis, and also olefins which are obtained by oligomerization of ethene or are obtainable via metathesis reactions or telomerization reactions.

Preferred starting materials are α-olefins in general, e.g. propene, 1-butene, 2-butene, 1-hexene, 1-octene and also dimers and trimers of butene (dibutene, di-n-butene, diisobutene, tributene).

The hydroformylation can be carried out continuously or batchwise. Examples of industrial apparatuses which can be employed are stirred vessels, bubble columns, jet nozzle reactors, tube reactors and loop reactors, some of which may be cascaded and/or provided with internals.

The reaction can be carried out in a single pass or in a plurality of stages. The separation of the aldehyde compounds formed and the catalyst can be carried out by conventional methods such as fractionation. This can be achieved industrially by, for example, distillation or use of a falling film evaporator or a thin film evaporator. These are particularly useful when the catalyst is separated off as a solution in a high-boiling solvent from the lower-boiling products. The catalyst solution which has been separated off can be used for further hydroformylations. When lower olefins (e.g. propene, butene, pentene) are used, discharge of the products from the reactor via the gas phase is also possible.

The following examples illustrate the present invention.

In all examples, the reactions were carried out under protective gas using standard Schlenk techniques. The solvents were dried over suitable desiccants prior to use.

Chlorine Compound A

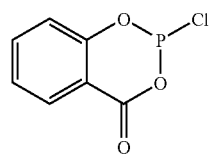

Chlorine compound A (2-chloro-4H-1,3,2-benzodioxaphosphorin-4-one) was procured from Aldrich, Taufkirchen, and used as supplied.

Chlorine Compound B

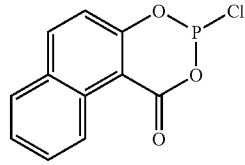

The chlorine compound B was prepared from 2-hydroxy-1-naphthalenecarboxylic acid using a method based on that of BE 667036, Farbwerke Hoechst AG, 1966; *Chem. Abstr.* 65 (1966) 13741d. The following description of the synthesis illustrates the procedure:

Reaction of 2-hydroxy-1-naphthalenecarboxylic acid with phosphorus trichloride 9.22 g (0.049 mol) of 2-hydroxy-1-naphthalenecarboxylic acid, 200 ml of dried toluene and 0.48 g (0.005 mol) of N-methyl-2-pyrrolidinone are placed in a 250 ml Schlenk tube. While stirring, 10.14 g (0.073 mol) of phosphorus trichloride are slowly added to this mixture. After connecting the Schlenk tube to an offgas line provided with a gas flowmeter, the reaction mixture is carefully heated to 95° C. and maintained at this temperature for 5 hours. To workup the reaction mixture, it is filtered and the solvent is removed from the filtrate under reduced pressure.

Yield: 11.01 g (44.6 mmol), corresponding to 91.0% of theory. $^{31}$P-NMR ($D_8$-toluene): δ 150.9 ppm Synthesis of the Phosphate Compound (A)

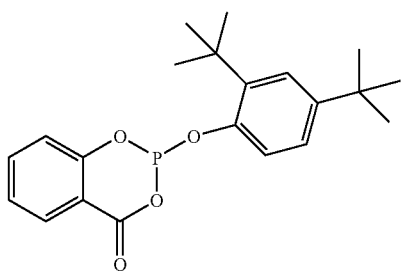

4.5 g of 2,4-di-tert-butylphenol (21.81 mmol) are dissolved in 100 ml of THF. 13.6 ml of a 1.6 mmol [sic] solution of n-butyllithium in hexane (21.81 mmol) are added dropwise to this solution at −20° C. The lithium phenoxide solution obtained is slowly added at 0° C. to 32.8 ml of a 0.665 M solution of the chlorine compound A (21.81 mmol) in THF and the resulting mixture is subsequently refluxed for 1 hour. After removal of the solvent under reduced pressure, 100 ml of hexane are added and the mixture is filtered. Removal of the solvent under reduced pressure gives an oily product.

Yield: 6.58 g (17.669 mmol), corresponding to 81.2% of theory Elemental analysis (calc. for $C_{21}H_{25}O_4P$; M=372.39 g/mol): C 68.05 (67.73); H 6.96 (6.77); P 7.98 (8.32)% $^{31}$P-NMR ($D_8$-toluene): δ 119.8 ppm. EI-MS (70 eV): 372 (38%, M$^+$), 357 (100%)

Synthesis of the Phosphate Compound (J)

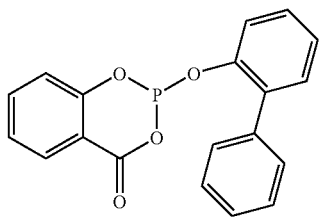

3.617 g of 2-phenylphenol (21.25 mmol) are dissolved in 100 ml of THF. 13.28 ml of a 1.6 M solution of n-butyllithium in hexane (21.25 mmol) are added dropwise to this solution at −20° C. The lithium phenoxide solution obtained is slowly added at 0° C. to 32.0 ml of a 0.665 M solution of the chlorine compound A (21.25 mmol) in THF and the resulting mixture is subsequently refluxed for 1 hour. After removal of the solvent under reduced pressure, 80 ml of toluene are added and the mixture is filtered. The filtrate is freed completely of solvent under reduced pressure. An oily product is obtained.

Yield: 5.80 g (17.24 mmol), corresponding to 81.7% of theory Elemental analysis (calc. for $C_{19}H_{13}O_4P$; M=336.28 g/mol): C 68.24 (67.86); H 4.02 (3.90); P 9.66 (9.21)% $^{31}$P-NMR ($CD_2Cl_2$): δ 118.4 ppm. EI-MS (70 eV): 335 (42%, M$^+$), 167 (100%, M$^+$-$OC_6H_4$- o-$C_6H_5$)

Synthesis of the Phosphite Compound (D)

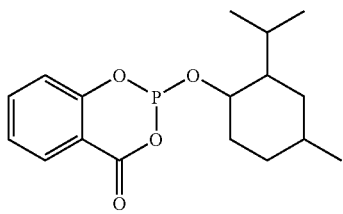

4.155 g of menthol (26.59 mmol) are dissolved in THF (100 ml) and admixed at −20° C. under argon with 16.6 ml of a 1.6 M solution of n-butyllithium in n-hexane (26.59 mmol). The lithium menthylate solution is warmed to room temperature and then added to a solution of 5.385 g of the chlorophosphorus compound A (26.59 mmol) in THF (30 ml) which has been cooled to 0° C. The reaction mixture is subsequently refluxed for 1 hour, evaporated to dryness under reduced pressure and the residue is taken up in 100 ml of hexane. Filtration and removal of the solvent under reduced pressure give the product as a light-yellow oil.

Yield: 6.48 g (20.1 mmol), corresponding to 75% of theory. $^{31}$P-NMR ($CD_2Cl_2$): δ 127.4 ppm. EI-MS (70 eV) m/e=323 (2%, M$^+$+H): 167 (33%); 138 (92%); 83 (100%).

Hydroformylation of 1-octene and di-n-butene Using the Phosphite Compounds (A), (J) and (D)

The hydroformylation experiments were carried out in a 200 ml autoclave from Buddeberg, Mannheim, equipped with a pressure maintenance device, gas flow measurement, sparging stirrer and pressure pipette. In the autoclave, 10 ml of a solution of rhodium in the form of [Rh(1,5-cyclooctadiene)acac] (acac=acetylacetonate anion) (0.604 mM in the case of 1-octene or 6.04 mM in the case of di-n-butene) as catalyst precursor were mixed under an argon atmosphere with the corresponding amount of the phosphite compound dissolved in toluene and made up to 41 ml with toluene. 15 ml of 1-octene or di-n-butene were introduced into the pressure pipette. After replacement of the argon atmosphere by flushing with synthesis gas (CO/H2=1:1), the rhodium/ligand mixture was heated while stirring (1500 rpm) to 100° C. in the case of 1-octene or 120° C. in the case of di-n-butene under a synthesis gas pressure of 30–33 bar in the case of 1-octene or 11–13 bar in the case of di-n-butene. After the desired reaction temperature had been reached, the synthesis gas pressure was increased to 50 bar in the case of 1-octene or 20 bar in the case of di-n-butene and olefin was added. The reaction was carried out under constant pressure (regulator from Bronkhorst (The Netherlands)) for 3 hours in the case of 1-octene or 6 hours in the case of di-n-butene. After the time of the experiment had elapsed, the autoclave was cooled to room temperature, depressurized and flushed with argon. 1 ml of the autoclave solution in the case of 1-octene or 2 ml in the case of di-n-butene was/were in each case admixed with 5 ml of n-pentane and analyzed by gas chromatography.

Experimental parameters for 1-octene:

Rhodium concentration=14 ppm, Rh:ligand:1-octene ratio=1:10:15700; T=100° C., p=50 bar of synthesis gas (CO/$H_2$=1:1), t=3 h, solvent:toluene Experimental parameters for di-n-butene:

Rhodium concentration=140 ppm, Rh:ligand:di-n-butene ratio=1:10:1570; T=130° C., p=20 bar of synthesis gas (CO/$H_2$=1:1), t=6 h, solvent:toluene

TABLE

Hydroformylation of 1-octene and di-n-butene

|  | Phosphite (A) | Phosphite (J) | Phosphite (D) |
|---|---|---|---|
| 1-Octene | | | |
| Yield (mol %) | 91 | 43 | 85 |
| n-selectivity (mol %) | 67.5 | 76.4 | 69.0 |
| Di-n-butene | | | |
| Yield (mol %) | 42 | 8 | 26 |
| n-selectivity (mol %) | 49.8 | 43.8 | 38.5 |

For the present purposes, the yield is the total yield of $C_9$-aldehydes. The n-selectivity is the ratio of terminally hydroformylated $C_9$-aldehydes to internally hydroformylated $C_9$-aldehydes.

The invention claimed is:

1. A phosphite of the formula I:

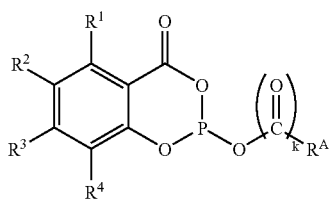

(I)

where $R^A$ is a monovalent unsubstituted aliphatic, alicyclic, aromatic, heteroaromatic, mixed aliphatic-alicyclic, mixed aliphatic-aromatic, heterocyclic, or mixed aliphatic-heterocyclic hydrocarbon radical having from 1 to 50 carbon atoms;

or a monovalent aromatic which is unsubstituted or substituted by at least one radical selected from among alicyclic, aromatic, heteroaromatic, mixed aliphatic-alicyclic, mixed aliphatic-aromatic, heterocyclic, mixed aliphatic-heterocyclic hydrocarbon radicals having from 1 to 25 carbon atoms, F, Cl, Br, I, -$CF_3$, -$CH_2$($CF_2$)$_j$$CF_3$ where j=0 —9, -$OR^9$, -$COR^9$, -$CO_2R^9$, -$CO_2M$, -$SR^9$, -$SO_3R^9$, -$SO_3M$, -$SO_2NR^9R^{10}$ or -$N=CR^9R^{10}$;

or a monovalent heteroaromatic which is unsubstituted or substituted by at least one radical selected from among aliphatic, alicyclic, aromatic, heteroaromatic, mixed aliphatic-alicyclic, mixed aliphatic-aromatic, heterocyclic, mixed aliphatic-heterocyclic hydrocarbon radicals having from 1 to 25 carbon atoms, F, Cl, Br, I, -$CF_3$, -$CH_2$($CF_2$)$_j$$CF_3$ where j=0 —9, -$OR^9$, -$COR^9$, -$CO_2R^9$, -$CO_2M$, -$SR^9$, -$SO_2R^9$, -$SOR^9$, -$SO_3M$, -$SO^2NR^9R^{10}$,-$NR^9R^{10}$ or -$N=CR^9R^{10}$.

$R^1$, $R^2$, $R^3$ and $R^4$ are each independently a monovalent substituted or unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radical having from 1 to 50 carbon atoms, H, F, Cl, Br, I, —$CF_3$, —$CH_2(CF_2)_jCF_3$ where j=0–9, —$OR^9$, —$COR^9$, —$CO_2R^9$, —$CO_2M$, —$SR^9$, —$SO_2R^9$, —$SOR^9$, —$SO_3R^9$, —$SO_3M$, —$SO_2NR^9R^{10}$, —$NR^9R^{10}$, —$N=CR^9R^{10}$, where $R^9$ and $R^{10}$ are each independently a H, monovalent substituted or unsubstituted aliphatic or aromatic hydrocarbon radical having from 1 to 25 carbon atoms, and M is an alkali metal ion, an alkaline earth metal ion, an ammonium ion or phosphonium ion;

or adjacent radicals $R^1$ to $R^4$ together form a fused substituted or unsubstituted aromatic, heteroaromatic, aliphatic, mixed aromaticaliphatic or mixed heteroaromatic-aliphatic ring system; and and k=0 or 1, wherein when $R^1$, $R^2$, $R^3$ and $R^4$ are each an H atom and k=0, $R^A$ is not an alkyl, aryl, aralkyl, alkenyl or cycloalkyl group, and when $R^1$, $R^2$, $R^3$ and $R^4$ are each an H atom and k=1, $R^A$ is not an alkyl or aryl group; or of the formula A, E, F, G, O or M:

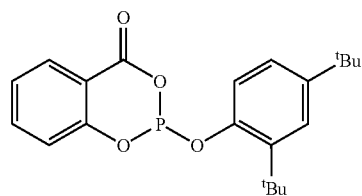

(A)

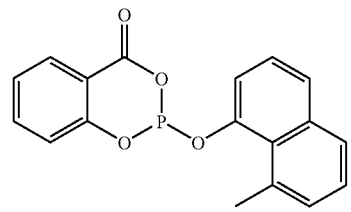

(E)

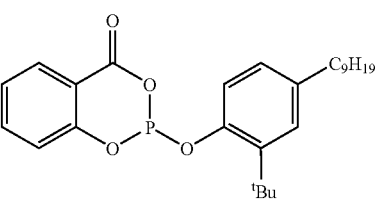

(F)

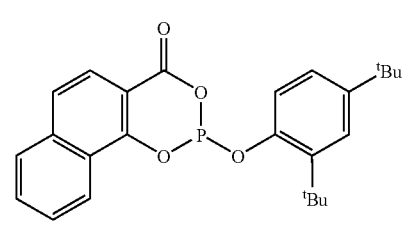

(G)

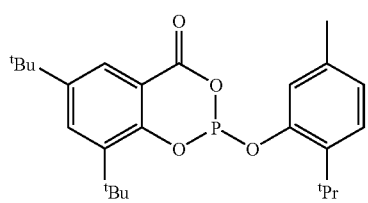

(M)

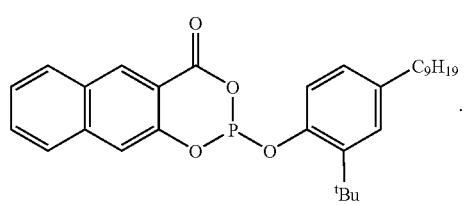

(O)

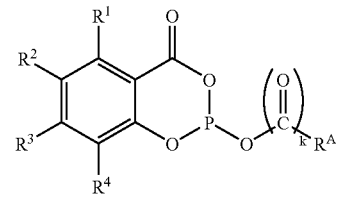

(I)

where $R^4$ is a monovalent substituted or unsubstituted aliphatic, alicyclic, aromatic, heteroaromatic, mixed aliphatic-alicyclic, mixed aliphatic-aromatic, heterocyclic and mixed aliphatic-heterocyclic hydrocarbon radical having from 1 to 50 carbon atoms;

$R^1$, $R^2$, $R^3$ and $R^4$ are each independently a monovalent substituted or unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radical having from 1 to 50 carbon atoms, H, F, Cl, Br, I, —$CF_3$, —$CH_2(CF_2)_jCF_3$ where j=0–9, —$OR^9$, —$COR^9$, —$CO_2R^9$, —$CO_2M$, —$SR^9$, —$SO_2R^9$, —$SOR_9$, —$SO_3R^9$, —$SO_3M$, —$SO_2NR^9R^{10}$, —$NR^9R^{10}$, —$N{=}CR^9R^{10}$, where $R^9$ and $R^{10}$ are each a H, monovalent substituted or unsubstituted aliphatic and aromatic hydrocarbon radical having from 1 to 25 carbon atoms and M is an alkali metal ion, an alkaline earth metal ion, an ammonium ion or phosphonium ion:

or adjacent radicals $R^1$ to $R^4$ together form a fused substituted or unsubstituted aromatic, heteroaromatic, aliphatic, mixed aromatic-aliphatic or mixed heteroaromatic-aliphatic ring system; and and k=0 or 1.

5. The phosphite-metal complex as claimed in claim 4, wherein the radical $R^4$ an aromatic or heteroaromatic group which may be unsubstituted or substituted by at least one of an aliphatic, alicyclic, aromatic, heteroaromatic, mixed aliphatic-alicyclic, mixed aliphaticaromatic, heterocyclic, mixed aliphatic-heterocyclic hydrocarbon radical having from 1 to 25 carbon atoms, F, Cl, Br, I, —$CF_3$, —$CH_2(CF_2)_j$ $CF_3$ where j=0–9, —$OR^1$, —$COR^9$, —$CO_2R^9$, —$CO_2M$, —$SR^9$, —$SO_2R^9$, —$SOR^9$, —$SO_3R^9$, —$SO_3M$, —$SO_2NR^9R^{10}$, —$NR^9R^{10}$ or —$N{=}CR^9R^{10}$.

6.

7. The phosphite-metal complex as claimed in claim 4, wherein adjacent radicals $R^1$ to $R^4$ together form a fused aromatic, heteroaromatic, aliphatic, mixed aromatic-aliphatic or mixed heteroaromatic-aliphatic ring system which is unsubstituted or is substituted by at least one of an aliphatic, alicyclic, aromatic, heteroaromatic, mixed aliphatic-alicyclic, mixed aliphatic-aromatic, heterocyclic, mixed aliphatic-heterocyclic hydrocarbon radical having from 1 to 50 carbon atoms, F, Cl, Br, I, —$CF_3$, —$CH_2(CF_2)_j$ $CF_3$ where j=0–9, —$OR^9$, —$COR^9$, —$CO_2R^9$, —$CO_2R^9$, —$CO_2M$, —$SR^9$, —$SO_2R^9$, —$SOR^9$, —$SO_3R^9$, —$SO_3M$, —$SO_2NR^9R^{10}$, —$NR^9R^{10}$ or —$N{=}CR^9R^{10}$.

8. The phosphite-metal complex as claimed in claim 4, wherein the metal is rhodium, platinum, palladium, cobalt or ruthenium.

2. The phosphite as claimed in claim 1, wherein $R^4$ is an aromatic or heteroaromatic group which have one or more aromatic, heteroaromatic, or aliphatic rings which are unsubstituted or substituted by at least one of an aliphatic, alicyclic, aromatic, heteroaromatic, mixed aliphatic-alicyclic, mixed aliphatic-aromatic, heterocyclic, mixed aliphatic-heterocyclic hydrocarbon radical having from 1 to 25 carbon atoms, F, Cl, Br, I, —$CF_3$, —$CH_2(CF_2)_jCF_3$ where j=0—9, —$OR^9$, —$COR^9$, —$CO_2R^9$, —$CO_2M$, —$SR^9$, —$SO_2R^9$, —$SOR^9$, —$SO_3R^9$, —$SO_3M$, —$SO_2NR^9R^{10}$, —$NR^9R^{10}$ or —$N{=}CR^9R^{10}$.

3. The phosphite as claimed in claim 1, wherein adjacent radicals $R^2$ to $R^4$ together form a fused aromatic, heteroaromatic, aliphatic, mixed aromatic-aliphatic or mixed heteroaromatic-aliphatic ring system which is unsubstituted or is substituted by at least one of an aliphatic, alicyclic, aromatic, heteroaromatic, mixed aliphatic-alicyclic, mixed aliphatic-aromatic, heterocyclic, mixed aliphatic-heterocyclic hydrocarbon radical having from 1 to 50 carbon atoms, F, Cl, Br, I, —$CF_3$, —$CH_2(CF_2)_jCF_3$ where j=0–9, —$OR^9$, —$COR^9$, —$CO_2R^9$, —$CO_2M$, —$SR^9$, —$SO_2R^9$, —$SOR^9$, —$SO_3R^9$, —$SO_3M$, —$SO_2NR^9R^{10}$, —$NR^9R^{10}$ or —$N{=}CR^9R^{10}$.

4. A phosphite-metal complex comprising a metal of group 4, 5, 6, 7, 8, 9 or 10 of the Periodic Table of the Elements and one or more phosphites of the formula I:

9. A process for the hydroformylation of olefins, which comprises;

reacting a monoolefin of monoolefin mixture with a mixture of carbon monoxide and hydrogen in the presence of a phosphite as defined in claim 1.

10. A process for preparing a phosphite, which comprises:

(a) reacting an α-hydroxyarylcarboxylic acid of the formula (1):

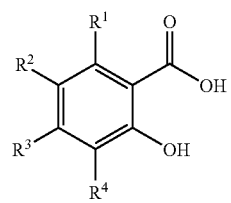

with PCL$_3$, PBr$_3$ or PI$_3$ in the presence of a base to form a halodioxaphosphorinone of the formula (2), where Hal=Cl, Br or I, and

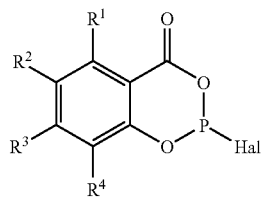

(b) reacting the halodioxaphosphorinone (2) on the presence of a base with (i) an alcohol Ho—R$^1$ to give a phosphite of the formula (I) in which k=0 or (ii) a carboxylic acid HOOC—R$^1$ to give a phosphite of the formula (I) in which k=1.

11. A process for preparing a phosphite-metal complex, which comprises:

reacting a metal of group 4, 5, 6, 7, 8, 9 or 10 of the Periodic Table in elemental form or in the form of a chemical compound with a phosphite of formula (I):

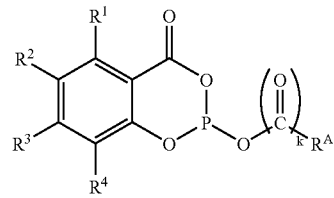

where R$^A$ is a monovalent substituted or unsubstituted aliphatic, alicyclic, aromatic, heteroaromatic, mixed aliphatic-alicyclic, mixed aliphatic-aromatic, heterocyclic and mixed aliphatic-heterocyclic hydrocarbon radical having from 1 to 50 carbon atoms, R$^1$, R$^2$, R$^3$ and R$^4$ are each selected independently from among a monovalent substituted or unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radical having from 1 to 50 carbon atoms, H, F, Cl, Br, I -CF$_3$, -CH$_2$(CF$_2$)jCF$_3$ where j=0—9, -OR$^9$, -COR$^9$-CO$_2$R$^9$, -CO$_2$M, -SR$^9$, -SOR$_2$, -SO$_3$R$^9$, -SO$_3$M, -SO$_2$NR$^9$R$^{10}$, -NR$^9$R$^{10}$, -N=CR$^9$R$^{10}$, where R$^9$ and R$^{10}$ are each a H, monovalent substituted or unsubstituted aliphatic and aromatic hydrocarbon radical having from 1 to 25 carbon atoms and M is an alkali metal ion, an alkaline earth metal ion, an ammonium ion or phosphonium ion, or adjacent radicals R$^1$ to R$^4$ together form a fused substituted or unsubstituted aromatic, heteroaromatic, aliphatic, mixed aromatic-aliphatic or mixed heteroaromatic-aliphatic ring system: and k=0 or 1.

12. A catalyst comprising the phosphite-metal complex as claimed in claim 4.

13. A method comprising carrying out the hydroformulation of one or more olefins in the presence of a phosphite-metal complex as claimed in claim 4.

14. A process for the hydroformulation of olefins, which comprises:

reacting a monoolefin or a monoolefin mixture with a mixture of carbon monoxide and hydrogen in the presence of a phosphite-metal complex as claimed in claim 4.

* * * * *